Sept. 24, 1957 C. H. PERKINS Plant Pat. 1,642
ROSE PLANT
Filed Jan. 7, 1957
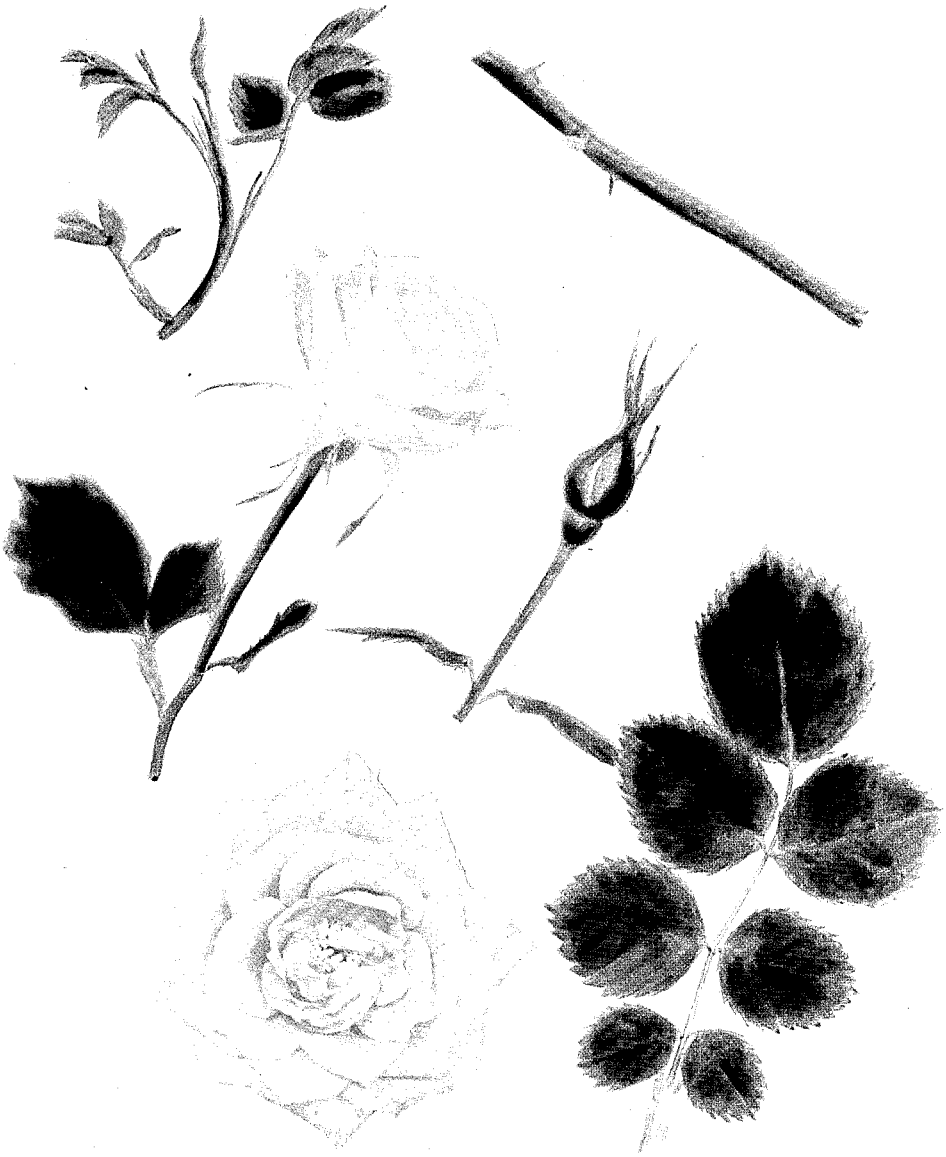
Inventor.
C. H. Perkins
By: Robert Cobb
Attorneys.

United States Patent Office

Plant Pat. 1,642

Patented Sept. 24, 1957

1,642

ROSE PLANT

Charles H. Perkins, Newark, N. Y., assignor to Jackson & Perkins Company, Newark, N. Y., a corporation of New York Application January 7, 1957, Serial No. 632,953

1 Claim. (Cl. 47—61)

The present invention relates to a new and distinct variety of rose plant of the large-flowered polyantha class, which was discovered by me as a sport of the variety "Garnette Supreme" (Plant Patent No. 1,318).

The new variety was discovered by me in the greenhouse benches of my assignee at Newark, New York, where plants of the variety "Garnette Supreme" were being grown under my supervision and direction. At the time of my discoverey, my attention was attracted thereto by the fact that one plant among the regular bench plants aforementioned exhibited at flower color that was different from the usual flower color of "Garnette Supreme," and in addition, the flowers exposed more of their centers and more stamens than was normal in the flowers of "Garnette Supreme." Upon closer observation, I found that the plant to which my attention had been attracted had sported, and I thereupon took steps to preserve the same, keep it under observation, and to later asexually reproduce the sport. These observations and asexual reproductions, as performed by both grafting and budding, at Newark, New York, and also at Pleasanton, California, conclusively established that the new color and form of the flowers of the sport were fixed and capable of being transmitted through succeeding propagations.

Except for the new characteristics described in the foregoing, the sport otherwise generally corresponds to its parent variety, but it is definitely distinguished therefrom, as well as from all other varieties of its class of which I am aware.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Sport of "Garnette Supreme."

Classification:

*Botanic.*—Large-flowered polyantha.

*Commercial.*—Floribunda.

*Flower*

(Observations made from specimens grown in a greenhouse at Newark, New York, in the early morning and in the early part of April.)

Blooming habit: Recurrent—continuous.

Bud:

*Size.*—Medium.

*Form.*—Ovoid; is not affected by wet or hot weather.

*Color.*—When sepals first divide—Spinel Red, Plate 26. When petals begin to unfurl—Tyrian Rose, Plate 12. When half-blown: inside of petals—Spinel Pink, Plate 26, lightly overcast with Deep Rose Pink, Plate 12, reverse of petals—Spinel Pink, Plate 26, lightly overcast with Tyrian Rose, Plate 12.

*Sepals.*—Slightly branched; with "hood" above bud; curl back when petals begin to unfurl. Color: inside—Pale Glass Green, Plate 31; outside—Light Bice Green, Plate 17.

*Calyx.*—Color—Light Bice Green, Plate 17. Shape—pear. Size — small. Aspect — smooth. Odor when rubbed—none.

*Peduncle.*—Length — medium. Aspect — smooth. Strength—erect; slender. Color — Light Bice Green, Plate 17.

*Opening.*—Opens up well; is not affected by adverse weather conditions.

Bloom:

*Size.*—Medium. Average size when fully expanded—from 2½ to 3 inches.

*Borne.*—Sometimes singly; sometimes several together; sometimes in irregular clusters.

*Stems.*—Medium length; strong.

*Form (when first open).*—Cupped. Permanence — flattens.

*Petalage.*—Double (full but open center); more of the flower center showing than in the parent variety "Garnette Supreme." Number of petals under normal conditions—from 35 to 40.

*Color.*—Center of flower — Eosine Pink, Plate 1. Outer petals—Thulite Pink, Plate 26, lightly overcast with Spinel Pink, Plate 26. Base of petals (aiglet)—Deep Sea-Foam Green, Plate 31. Inside of petals—Spinel Pink, Plate 26, with a very light overcast of Thulite Pink, Plate 26. Reverse of petals—Thulite Pink, Plate 26, lightly overcast with Rosolane Pink, Plate 26. General tonality from a distance—Spinel Pink, Plate 26.

*Discoloration.*—General tonality at end of first day—Spinel Pink, Plate 26. Second day—Spinel Pink, Plate 26, lightly overcast with Thulite Pink, Plate 26. Third day—Spinel Pink, Plate 26, overcast with Thulite Pink, Plate 26.

Petals:

*Texture.*—Leathery; thick; is not affected by wet or hot weather.

*Appearance.*—Inside—velvety. Outside—shiny.

*Form.*—Oval.

*Arrangement.* — Imbricated (regularly arranged shingle-like).

*Petaloids in center.*—Few; small.

*Persistence.*—Drop off cleanly.

*Fragrance.*—Moderate. Nature—tea (average hybird tea scent).

*Lasting quality.*—On the plant—long. As cut flower—very long.

*Genital organs*

Stamens, anthers: Medium size; many; regularly arranged around styles. Color—Apricot Yellow, Plate 4.

Stamens, filaments (threads): Short. Color—Picric Yellow, Plate 4.

Pollen: Color—Baryta Yellow, Plate 4.

Styles: Loosely separated; uneven length; medium length; thin.

Stigmas: Color—Maize Yellow, Plate 4.

Ovaries: All enclosed in calyx.

Hips: None.

Seeds: None.

*Plant*

Form: Bush.

Growth: Vigorous; upright.

Foliage: Compound of 5 to 7 leaflets.

*Size.*—Medium.

*Quantity.*—Normal.

*Color.*—New foliage: upper side—Acajou Red, Plate 13, with midrib of Yellowish Oil-Green, Plate 5; under side—Acajou Red, Plate 13, lightly overcast with Yellowish Oil-Green, Plate 5. Old foliage: upper side—Dark Cress Green, Plate 31; under side—Chromium Green, Plate 32.

*Shape.*—Oval pointed.

*Texture.*—Upper side — leathery. Under side — smooth.

*Ribs and veins.*—Ordinary.

*Edge.*—Serrated (saw-toothed).

*Serration.*—Both double and single; sharp.

*Leaf stem.*—Color—Absinthe Green, Plate 31. Under side—prickly.

*Stipules.*—Medium length; bearded.

Wood:

*New Wood.*—Color—Oil Green, Plate 5. Bark—smooth.

*Old wood.*—Color—Light Bice Green, Plate 17. Bark—smooth.

Thorns:

*Thorns.*—Quantity: on main stalks from base—ordinary; on laterals from stalk — ordinary.

Form—narrow base; some straight and some hooked downward. Color (when young)—Eosine Pink, Plate 1. Position—irregular.

*Prickles.*—Quantity: on main stalks—none; on laterals—none.

*Short needles.*—Quantity: on main stalks—none; on laterals—none.

I claim:

A new and distinct variety of rose plant of the large-flowered polyantha class, substantially as herein shown and described, characterized particularly as to novelty by its general similarity to its parent variety "Garnette Supreme" (Plant Patent No. 1,318), but being essentially distinguished therefrom by the general color tonality of its flowers of Spinel Pink very lightly overcast with Thulite Pink, and by the habit of its flowers of showing more of the flower center and stamens than in the flowers of the parent variety.

No references cited.